United States Patent
Levin et al.

(10) Patent No.: US 10,357,309 B2
(45) Date of Patent: Jul. 23, 2019

(54) ABLATION CURRENT MEASUREMENT

(71) Applicant: Biosense Webster (Israel) Ltd., Yokneam (IL)

(72) Inventors: Michael Levin, Haifa (IL); Avi Reuveni, Givat Shmuel (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 753 days.

(21) Appl. No.: 14/860,034

(22) Filed: Sep. 21, 2015

(65) Prior Publication Data

US 2017/0079712 A1 Mar. 23, 2017

(51) Int. Cl.
*A61B 18/14* (2006.01)
*A61B 18/00* (2006.01)

(52) U.S. Cl.
CPC ...... *A61B 18/1482* (2013.01); *A61B 18/1492* (2013.01); *A61B 2018/0072* (2013.01); *A61B 2018/00166* (2013.01); *A61B 2018/00357* (2013.01); *A61B 2018/00577* (2013.01); *A61B 2018/00642* (2013.01); *A61B 2018/00827* (2013.01); *A61B 2018/00839* (2013.01); *A61B 2018/00964* (2013.01); *A61B 2218/002* (2013.01)

(58) Field of Classification Search
CPC ............ A61B 18/1482; A61B 18/1492; A61B 2018/00636; A61B 2018/00827
See application file for complete search history.

(56) References Cited

U.S. PATENT DOCUMENTS

| | | | |
|---|---|---|---|
| 6,059,780 A | 5/2000 | Gough | |
| 6,161,543 A * | 12/2000 | Cox | A61B 18/1492 |
| | | | 128/898 |
| 2003/0187430 A1 | 10/2003 | Vorisek | |
| 2012/0123408 A1 | 5/2012 | Zoran | |
| 2012/0176103 A1* | 7/2012 | Lizarazo | G01R 15/06 |
| | | | 323/234 |
| 2012/0330305 A1* | 12/2012 | Zoran | A61B 18/1233 |
| | | | 606/41 |
| 2013/0156896 A1 | 6/2013 | Henze-Wethkamp | |
| 2013/0204111 A1* | 8/2013 | Flanders | A61B 5/0215 |
| | | | 600/407 |

(Continued)

FOREIGN PATENT DOCUMENTS

| | | |
|---|---|---|
| EP | 566726 A4 | 3/1994 |
| WO | 2013156896 A2 | 10/2013 |
| WO | WO 2013/156896 | 10/2013 |

OTHER PUBLICATIONS

Extended European Search Report for corresponding European patent application No. 16189715.2, dated Jan. 30, 2017.

*Primary Examiner* — Daniel W Fowler
*Assistant Examiner* — Bo Ouyang
(74) *Attorney, Agent, or Firm* — Notaro, Michalos & Zaccaria P.C.

(57) ABSTRACT

Ablation apparatus is provided. The apparatus includes an insertion tube, an ablation electrode disposed at a distal end of the tube, a conducting element, and a sensor. The conducting element conducts an ablating current from a proximal end of the tube to the ablation electrode, and the sensor measures an amplitude of the ablating current at the distal end of the tube. Other embodiments are also described.

18 Claims, 4 Drawing Sheets

(56) References Cited

U.S. PATENT DOCUMENTS

2013/0267943 A1* 10/2013 Hancock .............. A61B 18/042
                                                            606/33
2014/0243813 A1    8/2014 Paul
2014/0276755 A1    9/2014 Cao

* cited by examiner

ABLATION CURRENT MEASUREMENT

FIELD OF THE INVENTION

Embodiments of the present invention relate to ablation procedures, such as intracardiac ablation procedures, and associated systems and apparatus.

BACKGROUND

Minimally-invasive intracardiac ablation is the treatment of choice for various types of arrhythmias. To perform such treatment, the physician typically inserts a catheter through the vascular system into the heart, brings the distal end of the catheter into contact with myocardial tissue in areas of abnormal electrical activity, and then energizes one or more electrodes at or near the distal end in order to create tissue necrosis.

U.S. Pat. No. 6,059,780, whose disclosure is incorporated herein by reference, describes an ablation apparatus including a handpiece, an electrode extending from a handpiece distal end, a probe, a thermal sensor and an energy source. The electrode includes a distal end and a lumen, a cooling medium inlet conduit and a cooling medium exit conduit. Both conduits extend through the electrode lumen to an electrode distal end. A sidewall port, isolated from a cooling medium flowing in the inlet and outlet conduits, is formed in the electrode. The probe is at least partially positionable in the electrode lumen and configured to be advanced and retracted in and out of the sidewall aperture. The thermal sensor is supported by the probe. The electrode is coupled to an energy source.

European Application 0566726, whose disclosure is incorporated herein by reference, describes systems for ablating tissue that measure the current and voltage delivered to the associated electrode assembly and generate measured current and voltage signals. The systems divide the measured voltage signal by the measured current signal to derive a measured tissue impedance signal. The systems perform control functions based upon the measured tissue impedance signal.

International Application 2013/156896, whose disclosure is incorporated herein by reference, describes an energy application apparatus for applying energy to an object. An energy application unit applies energy to the object, wherein the energy application unit is adapted to use electrical current for applying the energy. A current measuring unit measures the electrical current used by the energy application unit and provides a signal being indicative of whether the energy is applied to the object based on the measured electrical current. The signal can be used by, for instance, a monitoring unit and/or a display unit for using and/or indicating the information whether energy is actually applied or not, without requiring a direct communication between the energy application unit and the monitoring unit and/or the display unit.

US 2003/0187430, whose disclosure is incorporated herein by reference, describes an electrode and a voltage-measurement reference device adapted to be positioned relative to a tissue load such that the load is generally located between the electrode and the reference device. A first wire and a second wire are electrically connected to the electrode. A power control system delivers RF current to the load through the first wire and measures the voltage across the load between the second wire and the reference device. The power control system measures the RF current through the first wire and determines the power delivered to the load using the measured current and voltage. The first and second wires function as thermocouple leads which, in combination with the electrode to which they are attached, form a thermocouple. The power control system monitors the voltage across the leads and determines the temperature at the electrode either during the delivery of current or alternatively, when current is not being delivered.

US 2014/0243813, whose disclosure is incorporated herein by reference, describes ablation systems and methods for providing feedback on lesion formation in real-time. The methods and systems assess absorptivity of tissue based on a degree of electric coupling or contact between an ablation electrode and the tissue. The absorptivity can then be used, along with other information, including, power levels and activation times, to provide real-time feedback on the lesions being created. Feedback may be provided, for example, in the form of estimated lesion volumes and other lesion characteristics. The methods and systems can provide estimated treatment times to achieve a desired lesion characteristic for a given degree of contact, as well as depth of a lesion being created. The degree of contact may be measured using different techniques, including the phase angle techniques and a coupling index.

SUMMARY OF THE INVENTION

There is provided, in accordance with some embodiments of the present invention, ablation apparatus. The apparatus includes an insertion tube, an ablation electrode disposed at a distal end of the tube, a conducting element, and a sensor. The conducting element conducts an ablating current from a proximal end of the tube to the ablation electrode, and the sensor measures an amplitude of the ablating current at the distal end of the tube.

In some embodiments, the sensor is further configured to harvest energy from the ablating current.

In some embodiments, the sensor is disposed within the tube.

In some embodiments, the sensor is disposed at the distal end of the tube.

In some embodiments, an outer diameter of the tube is less than 4 mm.

In some embodiments, the sensor is configured to measure the amplitude of the ablating current by measuring an amplitude of a voltage induced by a magnetic field that is produced by the ablating current.

In some embodiments, the sensor includes:
a magnetic core, through which the conducting element passes;
a coil wound around the core; and
circuitry, which is coupled to the coil, and is configured to measure the amplitude of the ablating current by measuring an amplitude of a voltage induced in the coil by a magnetic field in the core that is produced by the ablating current.

In some embodiments, the apparatus further includes a fluid-delivery tube, configured to deliver fluid from the proximal end of the insertion tube to the ablation electrode, passing through the magnetic core.

In some embodiments, an outer diameter of the core is less than 2 mm.

In some embodiments, the conducting element is wound one or more times around the magnetic core.

In some embodiments, the sensor is further configured to modulate onto the conducting element a feedback signal that is indicative of the measured amplitude of the induced voltage.

In some embodiments, the apparatus further includes receiving circuitry configured to ascertain, from the feedback signal, the amplitude of the induced voltage.

In some embodiments, the apparatus further includes a processor configured to estimate an amplitude of the ablating current, based on the amplitude of the induced voltage.

In some embodiments, the processor is further configured to control a generator of the ablating current, in response to the estimate.

There is further provided, in accordance with some embodiments of the present invention, a method for estimating an amplitude of an ablating current. An insertion tube, an ablation electrode disposed at a distal end of the tube, and a conducting element, configured to conduct an ablating current from a proximal end of the tube to the ablation electrode, are provided. The ablating current is passed over the conducting element, and an amplitude of the ablating current at the distal end of the tube is measured.

In some embodiments, the method further includes, prior to passing the ablating current over the conducting element, inserting the tube into a heart of a patient.

In some embodiments, measuring the amplitude of the ablating current includes using a sensor disposed within the tube to measure the amplitude.

In some embodiments, measuring the amplitude of the ablating current includes measuring the amplitude of the ablating current by measuring an amplitude of a voltage induced by a magnetic field that is produced by the ablating current.

In some embodiments, passing the ablating current over the conducting element includes passing the ablating current through a magnetic core, and measuring the amplitude of the ablating current includes measuring the amplitude of the ablating current by measuring an amplitude of a voltage induced by a magnetic field in the core that is produced by the ablating current.

In some embodiments, the method further includes modulating onto the conducting element a feedback signal that is indicative of the measured amplitude of the induced voltage.

In some embodiments, the method further includes controlling a generator of the ablating current, in response to measuring the amplitude of the ablating current.

There is further provided, in accordance with some embodiments of the present invention, a method for manufacturing ablation apparatus. An insertion tube is provided, an ablation electrode being disposed at a distal end of the tube. A conducting element is passed between a proximal end of the tube and the ablation electrode, the conducting element being configured to conduct an ablating current from the proximal end of the tube to the ablation electrode. A sensor is placed within the tube, the sensor being configured to measure an amplitude of the ablating current at the distal end of the tube.

In some embodiments, the sensor includes a magnetic core, and passing the conducting element between the proximal end of the tube and the ablation electrode includes passing the conducting element through the magnetic core.

In some embodiments, the method further includes winding the conducting element one or more times around the magnetic core.

In some embodiments, the method further includes passing a fluid-delivery tube, configured to deliver fluid from the proximal end of the insertion tube to the ablation electrode, through the magnetic core.

The present invention will be more fully understood from the following detailed description of embodiments thereof, taken together with the drawings, in which:

DETAILED DESCRIPTION OF EMBODIMENTS

Overview

When performing an ablation procedure, a catheter, comprising an insertion tube, is inserted into the patient's heart, and an ablation electrode disposed at the distal end of the tube is brought into contact with cardiac tissue of the patient. To ablate the tissue, an ablating current is then passed from a radiofrequency (RF) generator at the proximal end of the tube to the ablation electrode.

To ensure that the procedure is safely and effectively performed, it is advantageous for the operating physician to monitor the amplitude of the ablating current. One solution is to place a sensor at the proximal end of the tube, e.g., by integrating such a sensor with the RF generator. However, this solution may be suboptimal, in that, as the ablating current passes toward the distal end of the tube, some of the ablating current may be lost to parasitic capacitance, such that the amplitude of the ablating current that is actually delivered to the tissue may be less than the amplitude that is measured at the proximal end of the tube.

Embodiments of the present invention provide a different solution, by which the amplitude of the ablating current at the distal end of the tube is measured. In such embodiments, a sensor may be placed at or near the distal end of the tube, typically within the tube. The sensor may comprise, for example, a magnetic core, a coil wound around the core, and circuitry coupled to the coil. The conducting element (e.g., the wire) that delivers the ablating current to the ablation electrode passes through the magnetic core, such that a magnetic field is produced in the core by the ablating current. The magnetic field induces a voltage in the coil, and the circuitry measures the amplitude of the induced voltage. The amplitude of the ablating current may then be estimated, based on the amplitude of the induced voltage.

In general, as used within the claims and description of the present application, any reference to measurement of the ablating current may include within its scope any form of direct or indirect measurement. For example, the above-described estimation of the amplitude of the ablating current based on the amplitude of the induced voltage may be referred to as a measurement of the ablating current.

System Description

Figure 1:
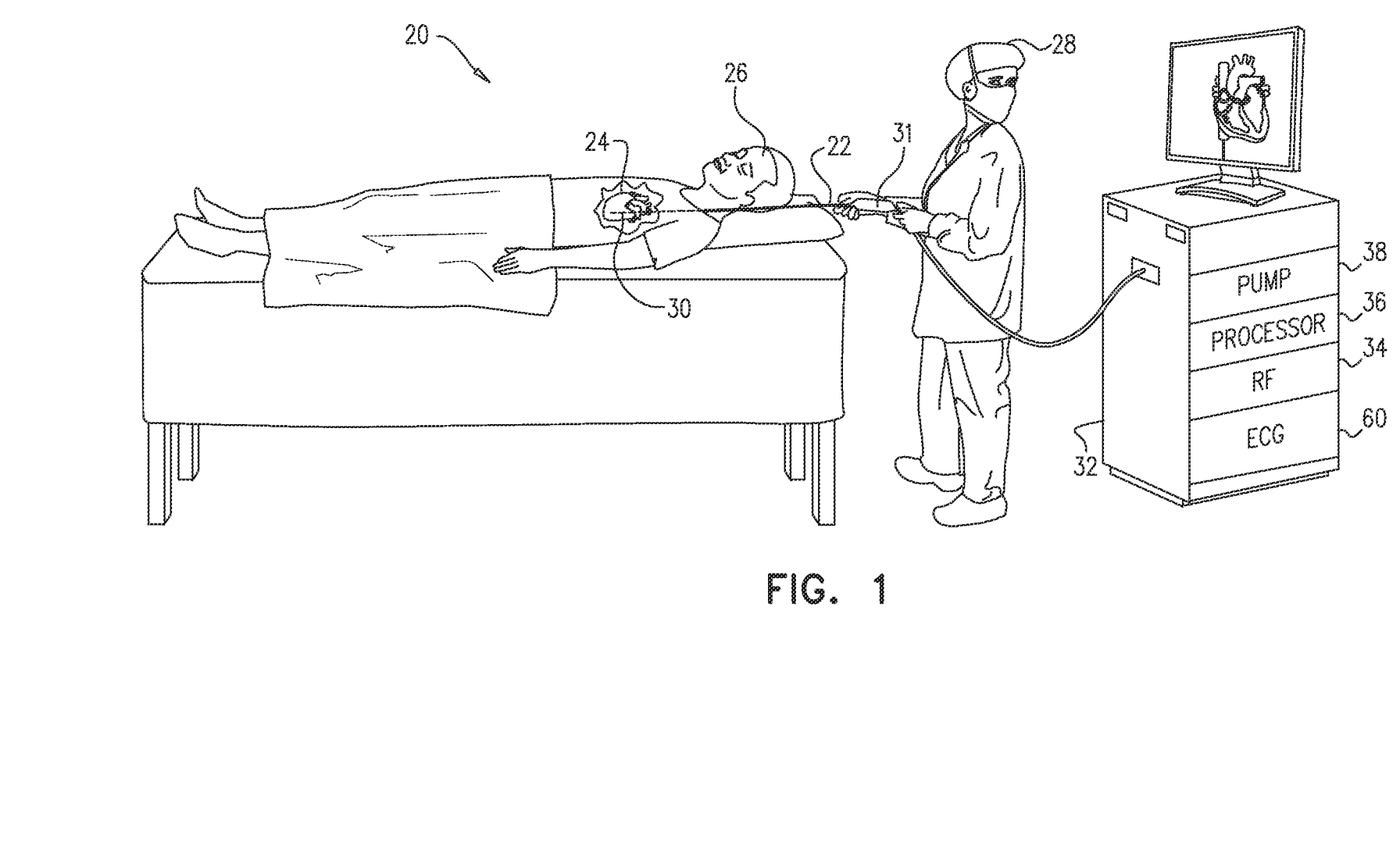
FIG. 1 is a schematic pictorial illustration of a system for cardiac ablation treatment, in accordance with an embodiment of the present invention.

Reference is initially made to FIG. 1, which is a schematic pictorial illustration of a system 20 for cardiac ablation treatment, in accordance with an embodiment of the present invention. An operator 28 (such as an interventional cardiologist) inserts an intra-body probe, such as a catheter 22, via the vascular system of a patient 26, into a chamber of the patient's heart 24. For example, to treat atrial fibrillation, the operator may advance the catheter into the left atrium and bring an ablation electrode 30 at a distal end of the catheter into contact with myocardial tissue that is to be monitored and/or ablated.

Catheter 22 is connected at its proximal end to a handle 31, which is connected, in turn, to a console 32. Console 32 comprises a radiofrequency (RF) generator 34, which supplies electrical power to ablation electrode 30 in order to ablate the target tissue. An irrigation pump 38 supplies an irrigating fluid, such as a saline solution, through catheter 22 to ablation electrode 30. (The irrigating fluid is then passed into the blood during the ablation procedure, in order to help prevent blood clots from forming.) A processor 36 may be used to monitor the ablating current and/or control the current by controlling RF energy generator 34, either automatically or in response to inputs from operator 28. Before, during, and/or after the procedure, an electrocardiogram (ECG) recorder 60 may record an ECG of the patient.

Figure 2A:
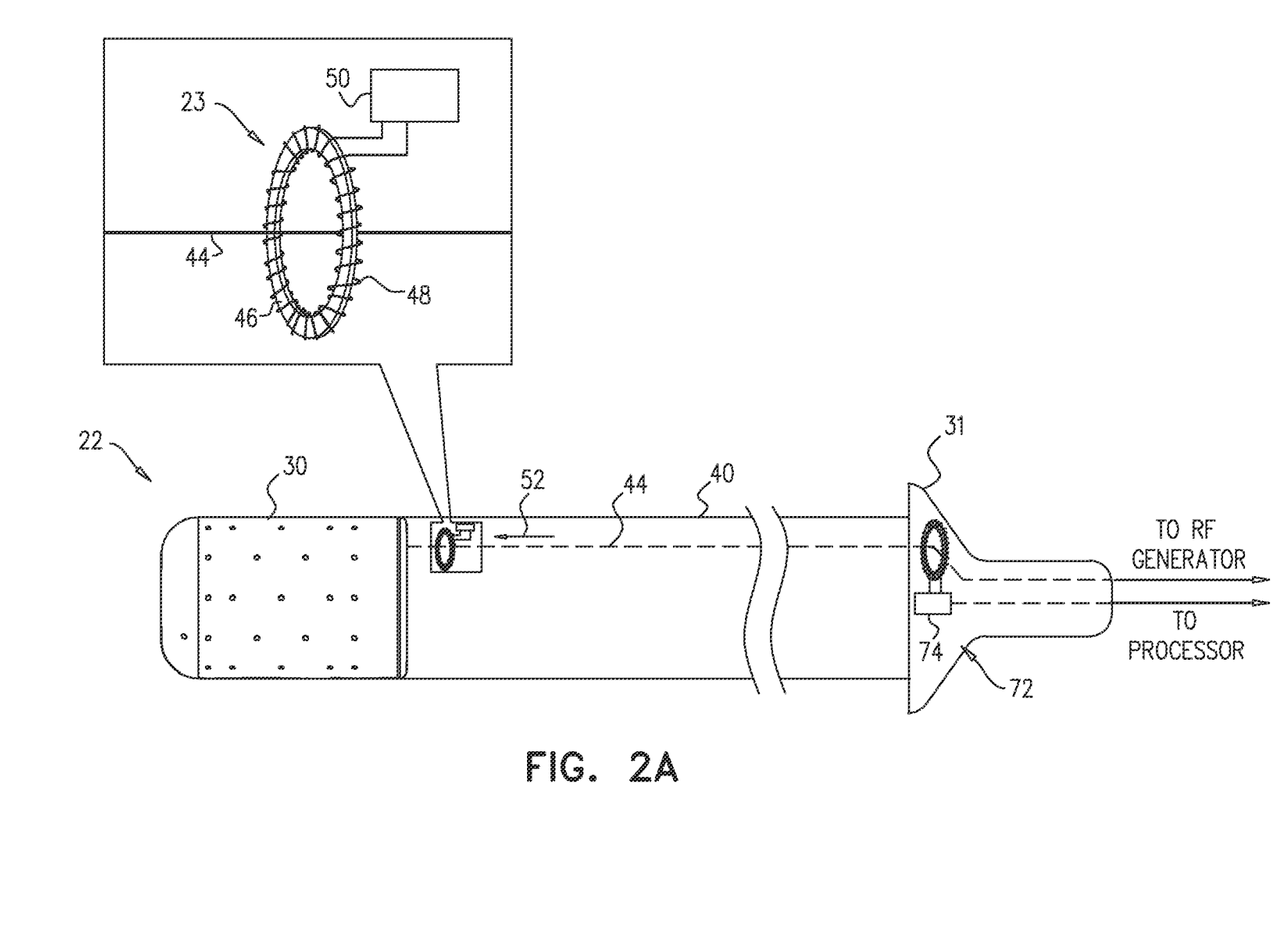
FIGS. 2A-B are schematic illustrations of a catheter, in accordance with some embodiments of the present invention.
Figure 2B:
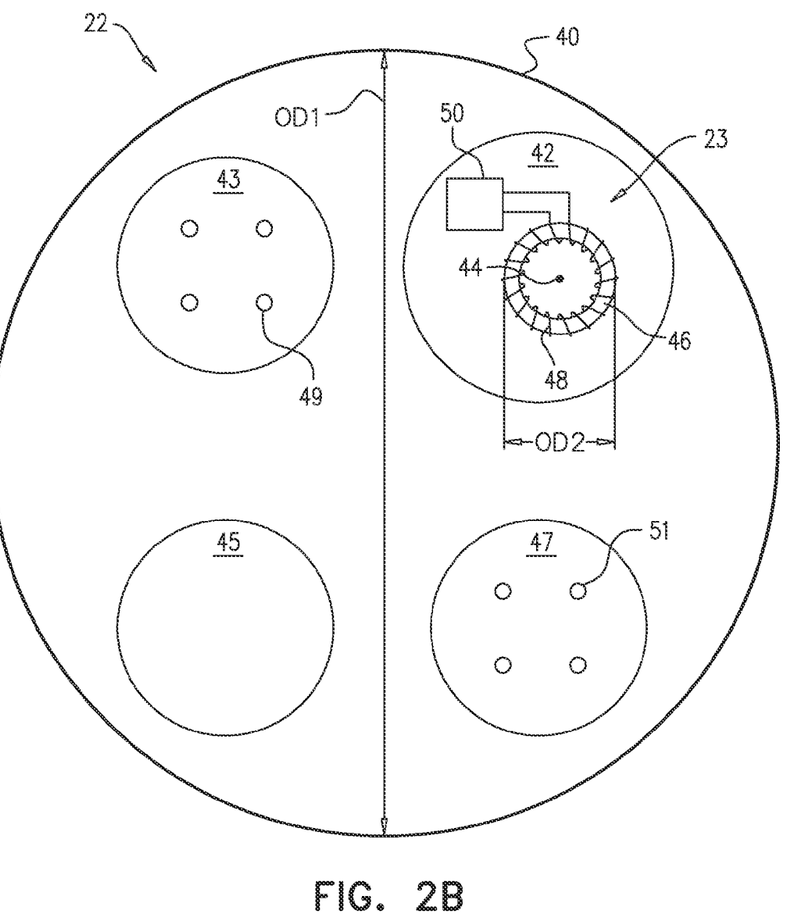

Reference is now made to FIGS. 2A-B, which are schematic illustrations of catheter 22, in accordance with some embodiments of the present invention. Catheter 22 comprises an insertion tube 40, having a proximal end and a distal end. Ablation electrode 30 is disposed at the distal end of the tube, and a conducting element (e.g., a wire) 44 is configured to conduct an ablating current 52 from the proximal end of the tube to the ablation electrode. For example, as shown in FIG. 2B, the insertion tube may be shaped to define a lumen 42, and conducting element 44 may run proximally-distally within lumen 42. A sensor 23 is configured to measure the amplitude of ablating current 52 at the distal end of the tube. Typically, sensor 23 is disposed at or near the distal end of the tube, typically within the tube. Sensor 23 may be embodied as shown in the figures and described hereinbelow. Alternatively, sensor 23 may comprise any other suitable current-measuring sensor.

In the particular embodiment shown in FIGS. 2A-B, sensor 23 comprises a magnetic core 46 (comprising, for example, a ferromagnetic material such as ferrite). Magnetic core 46 is typically disposed within the tube (e.g., within lumen 42), near the distal end of the tube, and conducting element 44 passes through magnetic core 46. As further shown in FIGS. 2A-B, sensor 23 further comprises a coil 48, which is wound around the core. (Typically, the coil is wound such that the resonant frequency of the resonant circuit formed by the inductance and parasitic capacitance of the coil is significantly higher than the frequency of ablating current 52.) As ablating current 52 passes through the magnetic core, the ablating current produces a magnetic field in the core, which in turn induces a voltage in coil 48. Circuitry 50, which is typically coupled to the coil, measures the induced voltage.

Typically, the outer diameter OD1 of tube 40 is less than 4 mm. For example, OD1 may be between 2 and 4 mm, e.g., approximately 3 mm. Embodiments of the present invention provide techniques for manufacturing core 46, coil 48, and circuitry 50, such that the above elements are sufficiently small to fit within the tube. For example, the outer diameter OD2 of the core may be less than 2 mm, e.g., between 1 and 1.5 mm. The scope of the present invention includes shaping the core as a circle, ellipse, or any other suitable shape, and aligning the core in any suitable orientation with respect to the longitudinal axis of the tube.

In some embodiments, insertion tube 40 is further shaped to define one or more lumens, in addition to lumen 42. For example, the insertion tube may be shaped to define an irrigating-fluid lumen 45, configured to deliver irrigating fluid from pump 38 (FIG. 1) to the ablation electrode. The insertion tube may be further shaped to define a control-wire lumen 43, along which one or more control wires 49 run; control wires 49 may be manipulated, via handle 31, to steer and/or otherwise control the catheter. In some embodiments, the catheter further comprises magnetic location sensors at the distal end of the catheter. In such embodiments, the insertion tube may be further shaped to define a magnetic-sensor-wire lumen 47, along which run wires 51 that are connected to the magnetic navigation sensors. Typically, magnetic core 46 is placed far enough away from the location sensors—e.g., at least 10 mm from the location sensors—such that the magnetic core and the location sensors do not interfere with each other.

In some embodiments, the tube is not shaped to define a dedicated irrigating-fluid lumen. Instead, a fluid-delivery tube, which delivers irrigating fluid from pump 38, passes through the magnetic core. Such embodiments may allow space within the insertion tube to be used more efficiently.

In general, it is noted that the scope of the present invention includes having any suitable number of distinct lumens within the insertion tube, along with any suitable numbers or types of wires, tubes, or other elements disposed within the lumens.

In some embodiments, conducting element 44 is wound one or more times around magnetic core 46. To estimate the amplitude of the ablating current, the measured amplitude of the induced voltage may be multiplied by a coefficient that is a function of, at least, (i) the number of windings of the conducting element around the core, and (ii) the number of windings of coil 48 around the core. (If conducting element 44 is not wound around the magnetic core, the value of (i) that is used is one half.)

Figure 3:
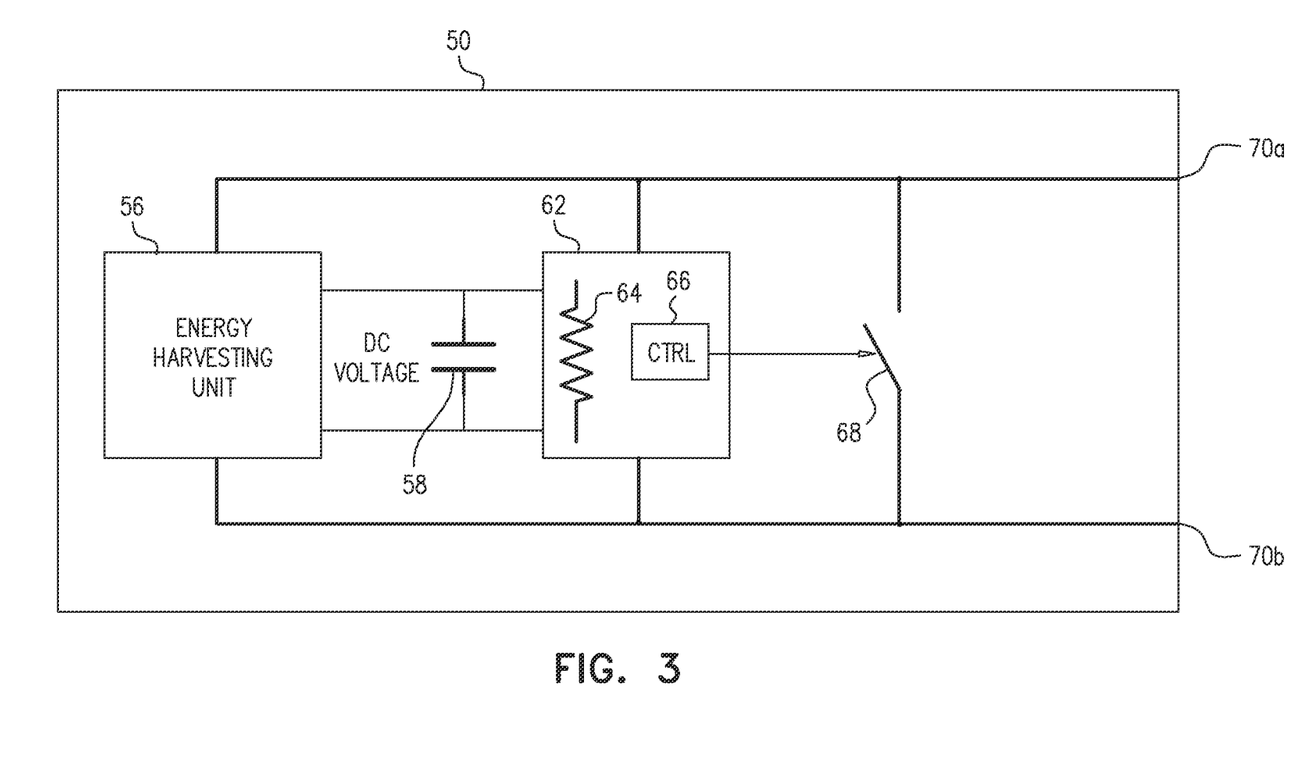
FIG. 3 is a schematic illustration of a sensor, in accordance with some embodiments of the present invention.

Reference is now additionally made to FIG. 3, which is a schematic illustration of circuitry 50, in accordance with some embodiments of the present invention. Circuitry 50 comprises inputs 70a and 70b, which are configured to receive the two ends of coil 48, as shown in FIGS. 2A-B. Circuitry 50 further comprises a measurement unit 62, configured to measure the induced voltage in the coil. For example, measurement unit 62 may comprise a voltmeter, configured to measure the induced voltage across a resistor 64. (The exact configuration of circuitry within the measurement unit is not shown in FIG. 3.)

Typically, measurement unit 62 further comprises a controller (CTRL) 66, such as the STM32L151RE™ microcontroller from ST™. By controlling a switch 68 (e.g., a bipolar MOSFET switch), controller 66 modulates the current on conducting element 44, at a frequency different from the frequency of the ablating current, to indicate the measured amplitude of the induced voltage. In this manner, the sensor modulates onto the conducting element a feedback signal that is indicative of the measured amplitude of the induced voltage.

Typically, the modulation is detected by receiving circuitry 72. Receiving circuitry 72 may be disposed at the proximal end of the catheter, such as within handle 31, as depicted in FIG. 2A, or within console 32 (FIG. 1). The receiving circuitry ascertains, from the feedback signal, the amplitude of the induced voltage. Typically, receiving circuitry 72 then communicates the amplitude of the induced voltage to processor 36 (FIG. 1), which estimates the amplitude of the ablating current based on the amplitude of the induced voltage. In response to the estimate, the processor may then control RF generator 34, e.g., by increasing or decreasing the power supplied by the generator. Alternatively or additionally, the processor may generate an output indicative of the estimate, and operator 28 (FIG. 1) may control the generator in response thereto.

Typically, circuitry 50 further comprises an energy-harvesting unit 56, such as, for example, the LTC3330™ unit from Linear Technology™, or the MAX17710™ unit from MAXIM™. Energy-harvesting unit 56 harvests energy from the ablating current, by rectifying the induced alternating-current (AC) voltage, and using the rectified direct-current (DC) voltage to charge a storage capacitor 58, which then powers measurement unit 62. In such embodiments, it may not be necessary to supply the sensor with a battery or other dedicated power source, since the energy harvested from the ablating current may be sufficient to power the sensor. (It is noted that the energy harvested from the ablating current is typically only a small part of the total energy delivered by the ablating current, such that the harvesting of energy from the ablating current does not reduce the efficacy of the ablation procedure.)

Typically, the receiving circuitry comprises a current transformer, comprising circuitry 74 that comprises, for example, a preamplifier, a demodulator, a decoder, and/or other electronic components. The preamplifier amplifies the received signal for the demodulator, which then filters out, from the received signal, the ablation-current frequency. The decoder, typically comprising a microcontroller such as the aforementioned STM32L151RE™ controller, then ascertains the amplitude of the induced voltage, and communicates with the processor, as described hereinabove.

In alternative embodiments, the processor, rather than the receiving circuitry, ascertains the amplitude of the induced voltage from the feedback signal.

In some embodiments, the sensor uses a different method from the method described above to provide feedback to the receiving circuitry. For example, the sensor may use capacitive coupling to transmit a feedback signal over a separate conducting element.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. Ablation apparatus, comprising:
an insertion tube;
an ablation electrode disposed at a distal end of the tube;
a conducting element, configured to conduct an ablating current from a proximal end of the tube to the ablation electrode; and
a sensor configured to measure an amplitude of the ablating current at the distal end of the tube,
wherein the sensor is configured to measure the amplitude of the ablating current by measuring an amplitude of a voltage induced by a magnetic field that is produced by the ablating current,
wherein the sensor comprises:
a magnetic core, through which the conducting element passes;
a coil wound around the core; and
circuitry, which is coupled to the coil, and is configured to measure the amplitude of the ablating current by measuring an amplitude of a voltage induced in the coil by a magnetic field in the core that is produced by the ablating current, wherein the circuitry further comprises a measurement unit configured to measure the induced voltage in the coil,
wherein the coil is wound such that a resonant frequency of a resonant circuit formed by inductance and parasitic capacitance of the coil is higher than the frequency of the ablating current,
further comprising a storage capacitor configured to power the measurement unit, wherein the sensor is further configured to harvest energy from the ablating current, by rectifying the induced voltage and using the rectified voltage to charge the storage capacitor configured to power measurement unit,
wherein the sensor is further configured to modulate onto the conducting element a feedback signal that is indicative of the measured amplitude of the induced voltage, and
further comprising receiving circuitry configured to ascertain, from the feedback signal, the amplitude of the induced voltage, wherein the receiving circuitry comprises a current transformer, the current transformer comprising circuitry, the circuitry of the current transformer comprising, a preamplifier, a demodulator, a decoder, wherein the preamplifier is configured to amplify a received signal for the demodulator, wherein the demodulator is configured to filter out, from the received signal, the ablation current frequency, wherein the decoder, comprises a microcontroller the microcontroller adapted to ascertain the amplitude of the induced voltage, and to communicate with the processor.

2. The apparatus according to claim 1, wherein the sensor is disposed within the tube.

3. The apparatus according to claim 2, wherein the sensor is disposed at the distal end of the tube.

4. The apparatus according to claim 2, wherein an outer diameter of the tube is less than 4 mm.

5. The apparatus according to claim 1, further comprising a fluid-delivery tube, configured to deliver fluid from the proximal end of the insertion tube to the ablation electrode, passing through the magnetic core.

6. The apparatus according to claim 1, wherein an outer diameter of the core is less than 2 mm.

7. The apparatus according to claim 1, wherein the conducting element is wound one or more times around the magnetic core.

8. The apparatus according to claim 1, further comprising a processor configured to estimate the amplitude of the ablating current, based on the amplitude of the induced voltage.

9. The apparatus according to claim 8, wherein the processor is further configured to control a generator of the ablating current, in response to the estimate.

10. A method for estimating an amplitude of an ablating current, the method comprising:
providing (i) an insertion tube, (ii) an ablation electrode disposed at a distal end of the tube, (iii) a conducting element, configured to conduct an ablating current from a proximal end of the tube to the ablation electrode and (iv) a sensor configured to measure an amplitude of the ablating current at the distal end of the tube,
wherein the sensor is configured to measure the amplitude of the ablating current by measuring an amplitude of a voltage induced by a magnetic field that is produced by the ablating current,
wherein the sensor comprises:
a magnetic core, through which the conducting element passes;
a coil wound around the core; and
circuitry, which is coupled to the coil, and is configured to measure the amplitude of the ablating current by measuring an amplitude of a voltage induced in the coil by a magnetic field in the core that is produced by the ablating current, wherein the circuitry further comprises a measurement unit configured to measure the induced voltage in the coil,
wherein coil is wound such that a resonant frequency of a resonant circuit formed by inductance and parasitic capacitance of the coil is higher than the frequency of the ablating current,
further comprising a storage capacitor configured to power the measurement unit, wherein the sensor is further configured to harvest energy from the ablating current, by rectifying the induced voltage, and using the rectified voltage to charge the storage capacitor configured to power measurement unit,
wherein the sensor is further configured to modulate onto the conducting element a feedback signal that is indicative of the measured amplitude of the induced voltage, and
further comprising receiving circuitry configured to ascertain, from the feedback signal, the amplitude of the induced voltage, wherein the receiving circuitry comprises a current transformer, the current transformer comprising circuitry, the circuitry of the current transformer comprising, a preamplifier, a demodulator, a decoder, wherein the preamplifier is configured to amplify a received signal for the demodulator, wherein the demodulator is configured to filter out, from the received signal, the ablation current frequency, wherein the decoder, comprises a microcontroller the microcontroller adapted to ascertain the amplitude of the induced voltage, and to communicate with the processor;
passing the ablating current over the conducting element; and
measuring an amplitude of the ablating current at the distal end of the tube.

11. The method according to claim 10, further comprising, prior to passing the ablating current over the conducting element, inserting the tube into a heart of a patient.

12. The method according to claim 10, wherein measuring the amplitude of the ablating current comprises using a sensor disposed within the tube to measure the amplitude.

13. The method according to claim 10, wherein measuring the amplitude of the ablating current comprises measuring the amplitude of the ablating current by measuring an amplitude of a voltage induced by a magnetic field that is produced by the ablating current.

14. The method according to claim 13, wherein passing the ablating current over the conducting element comprises passing the ablating current through a magnetic core, and wherein measuring the amplitude of the ablating current comprises measuring the amplitude of the ablating current by measuring an amplitude of a voltage induced by a magnetic field in the core that is produced by the ablating current.

15. The method according to claim 13, further comprising modulating onto the conducting element a feedback signal that is indicative of the measured amplitude of the induced voltage.

16. The method according to claim 10, further comprising controlling a generator of the ablating current, in response to measuring the amplitude of the ablating current.

17. A method for manufacturing ablation apparatus, the method comprising:
providing an insertion tube, an ablation electrode being disposed at a distal end of the tube;
passing a conducting element between a proximal end of the tube and the ablation electrode, the conducting element being configured to conduct an ablating current from the proximal end of the tube to the ablation electrode; and
placing a sensor within the tube, the sensor being configured to measure an amplitude of the ablating current at the distal end of the tube,
wherein the sensor includes a magnetic core, and wherein passing the conducting element between the proximal end of the tube and the ablation electrode comprises passing the conducting element through the magnetic core,
winding the conducting element one or more times around the magnetic core,
coupling circuitry to the conducting element, said circuitry being configured to measure the amplitude of the ablating current by measuring an amplitude of a voltage induced in the coil by a magnetic field in the core that is produced by the ablating current, wherein the circuitry further comprises a measurement unit configured to measure the induced voltage in the coil,
wherein the conducting element is wound such that a resonant frequency of a resonant circuit formed by inductance and parasitic capacitance of the coil is higher than the frequency of the ablating current,
providing a storage capacitor configured to power the measurement unit, wherein the sensor is further configured to harvest energy from the ablating current, by rectifying the induced voltage and using the rectified voltage to charge the storage capacitor configured to power measurement unit,
wherein the sensor is further configured to modulate onto the conducting element a feedback signal that is indicative of the measured amplitude of the induced voltage, and
providing receiving circuitry configured to ascertain, from the feedback signal, the amplitude of the induced voltage, wherein the receiving circuitry comprises a current transformer, the current transformer comprising circuitry, the circuitry of the current transformer comprising, a preamplifier, a demodulator, a decoder, wherein the preamplifier is configured to amplify a received signal for the demodulator, wherein the demodulator is configured to filter out, from the received signal, the ablation current frequency, wherein the decoder, comprises a microcontroller the microcontroller adapted to ascertain the amplitude of the induced voltage, and to communicate with the processor.

18. The method according to claim 17, further comprising passing a fluid-delivery tube, configured to deliver fluid from the proximal end of the insertion tube to the ablation electrode, through the magnetic core.

* * * * *